Figure 1:
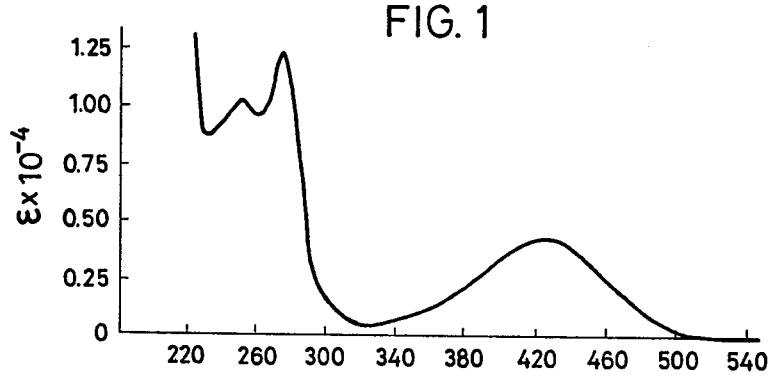

United States Patent [19]
Omura et al.

[11] 4,196,266
[45] Apr. 1, 1980

[54] PRODUCTION OF NANAOMYCIN A AND DERIVATIVES THEREOF

[75] Inventors: Satoshi Omura, Tokyo; Haruo Tanaka, Machida; Juichi Awaya, Souka; Toju Hata, Tokyo, all of Japan

[73] Assignee: The Kitasato Institute (Kitasato Kenkyuosho), Tokyo, Japan

[21] Appl. No.: 858,215

[22] Filed: Dec. 7, 1977

Related U.S. Application Data

[63] Continuation of Ser. No. 719,744, Sep. 2, 1976, abandoned, which is a continuation-in-part of Ser. No. 558,563, Mar. 14, 1975, abandoned.

[30] Foreign Application Priority Data

Apr. 28, 1976 [JP] Japan .................................. 51-49224

[51] Int. Cl.² .................................................. C12D 9/14
[52] U.S. Cl. .................................... 435/125; 435/127; 435/129; 435/132; 435/146; 435/147; 435/156; 435/169; 435/886; 260/345.2; 424/181
[58] Field of Search ......................... 195/80 R, 81, 96; 260/345.2; 424/181

[56] References Cited

U.S. PATENT DOCUMENTS

3,300,382 1/1967 Bergy et al. ..................... 195/80 R

OTHER PUBLICATIONS

Tanaka et al., Nanaomycins, New Antibiotics Produced by a Strain of Streptomyces, The Journal of Antibiotics, vol. 28, No. 12, Dec. 1975, (pp. 925–930).
Tanaka et al., Nanaomycins, New Antibiotics Produced by a Strain of Streptomyces, The Journal of Antibiotics, vol. 28, No. 11, Nov. 1975 (pp. 868–875).

*Primary Examiner*—David M. Naff
*Attorney, Agent, or Firm*—Wolder, Gross & Yavner

[57] ABSTRACT

The present invention relates to new compound nanaomycin A and derivatives thereof represented by general formula:

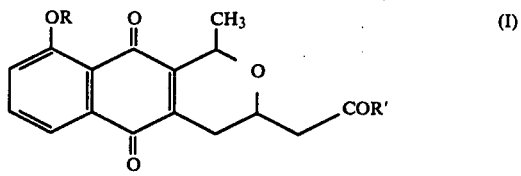

(I)

in which
(a) R is H and R' is OH (nanaomycin A),
(b) R is H and R' is NH₂ (nanaomycin C),
(c) R is COCH₃ and R' is CH (acetylnanaomycin A), and
(d) R is H and R' is OCH₃ (nanaomycin A methyl ester).

Nanaomycin A is a new compound of quinone type and its acute toxicity (LD₅₀, intra-penetrial injection) in mice is 28.2 mg/Kg. Nanaomycin A and derivatives thereof are active on Gram-positive bacteria, trichophyton and mycoplasma and are useful as a medicament for humans and animals. Nanaomycins A and C are produced by culturing a nanaomycin-producing strain belonging to the genus Streptomyces aerobically in a medium to accumulate nanaomycins A and C in the cultured broths. The derivatives acetylnanaomycin A and nanaomycin A methyl ester have similar properties to those of nanaomycin A.

4 Claims, 10 Drawing Figures

PRODUCTION OF NANAOMYCIN A AND DERIVATIVES THEREOF

RELATED APPLICATION

This application is a continuation of application Ser. No. 719,744, filed Sept. 2, 1976, which is a continuation-in-part of application Ser. No. 558,563, filed Mar. 14, 1975, both now abandoned.

SUMMARY OF THE INVENTION

The present invention relates to new compound designated as nanaomycin A which is also designated as OS-3966-A or Rosanomycin A. and derivatives thereof represented by general formula:

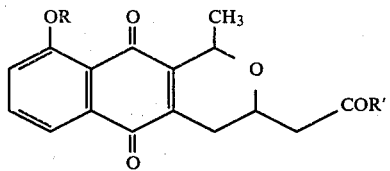

in which
(a) R is H and R' is OH,
(b) R is H and R' is NH$_2$,
(c) R is COCH$_3$ and R' is OH, and
(d) R is H and R' is OCH$_3$.

In this specification, the compounds of general formula (I)-(a), -(b), -(c) and -(d) are designated as nanaomycin A, nanaomycin C, acetylnanaomycin A and nanaomycin A methyl ester, respectively. The above-mentioned formula has been determined by various experiments including nuclear magnetic resonance spectra, elementary analysis, mass-spectra and the like.

DRAWINGS

FIG. 1—UV absorption spectrum of nanaomycin A

Figure 2:
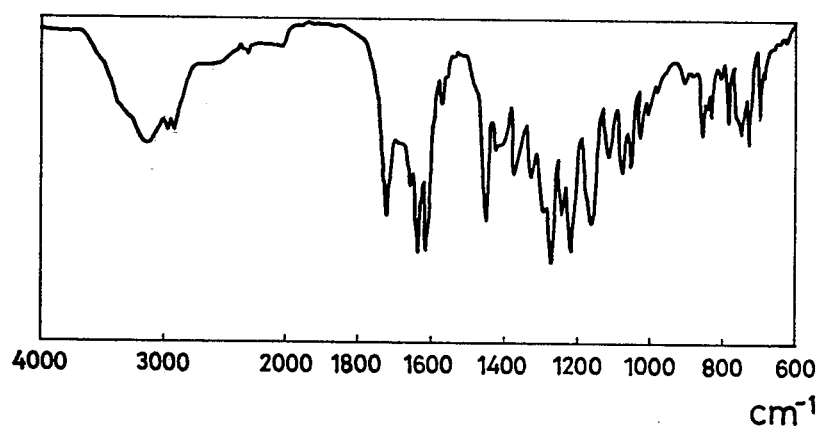

FIG. 2—IR absorption spectrum of nanaomycin A

Figure 3:
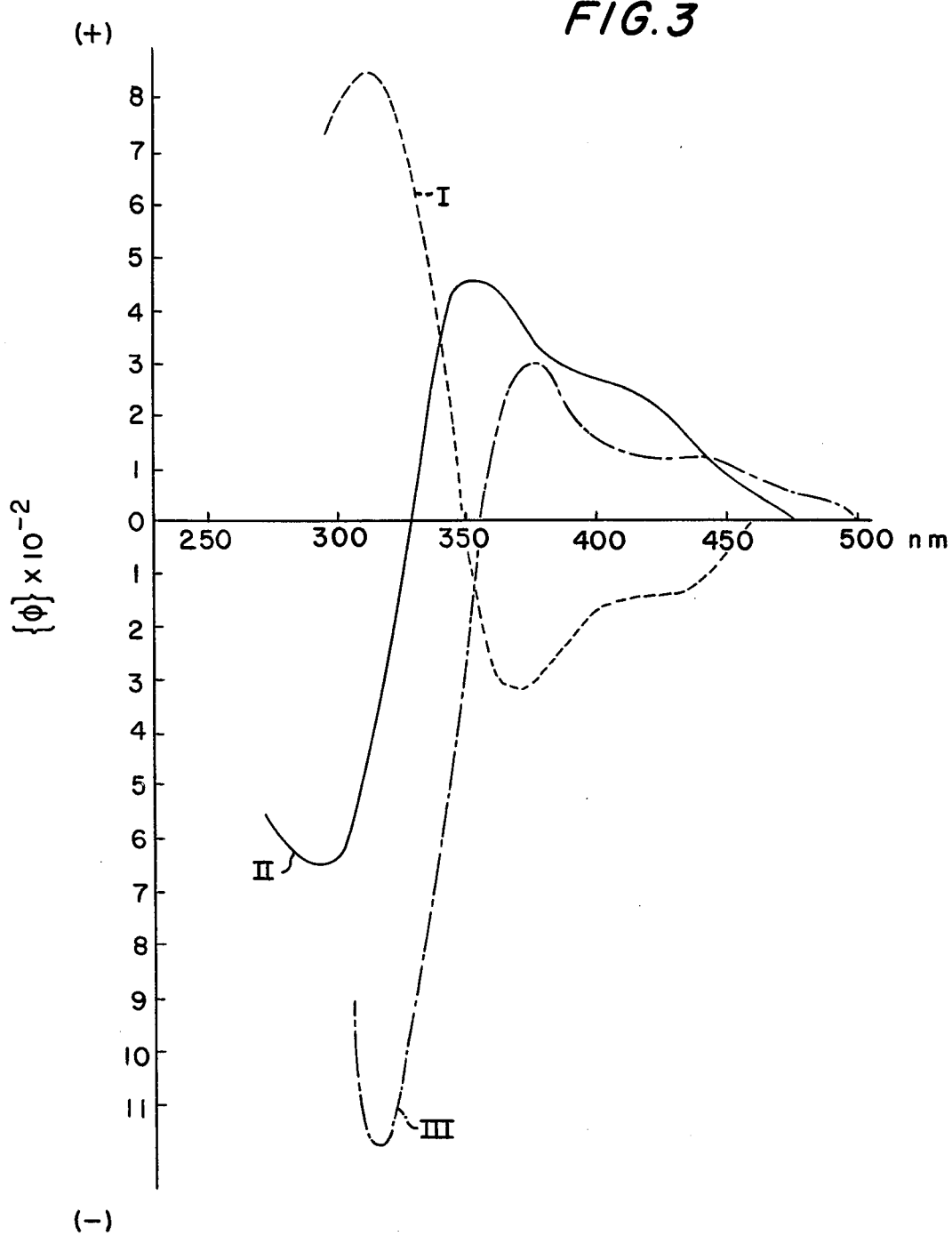
Figure 4:
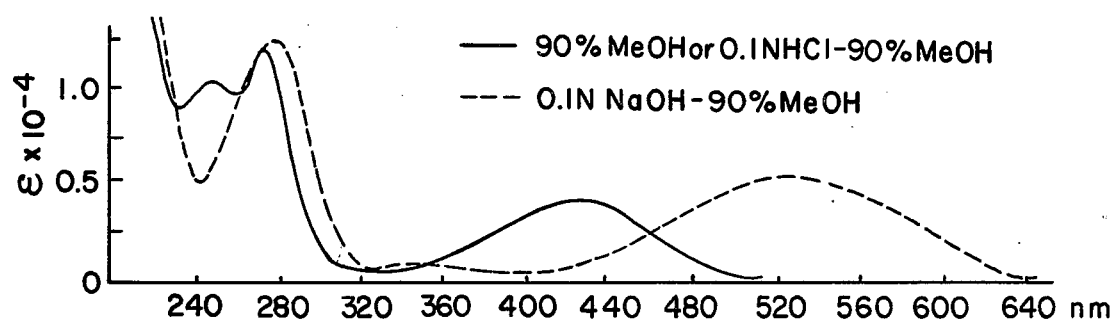
Figure 5:
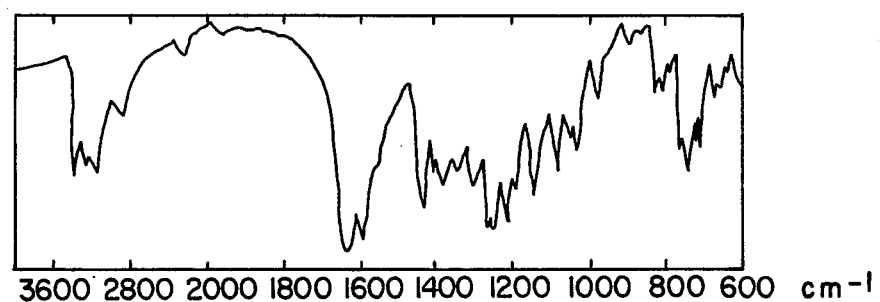
Figure 6:
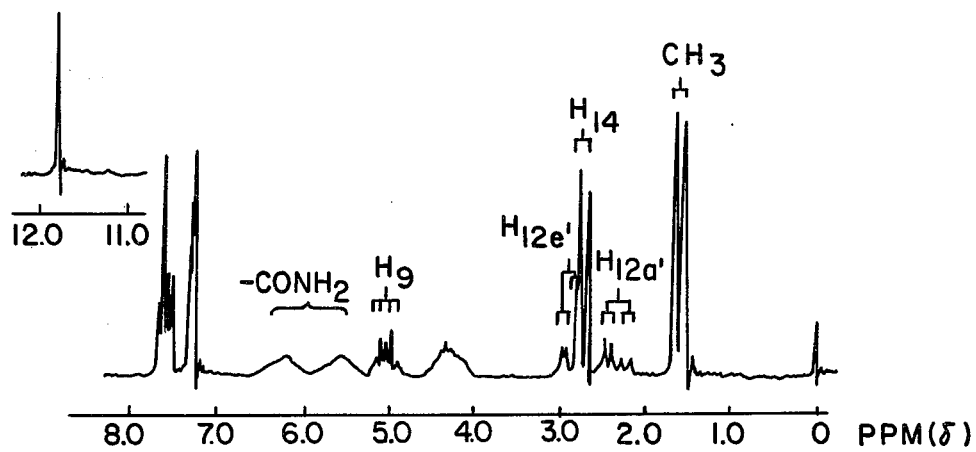
Figure 7:
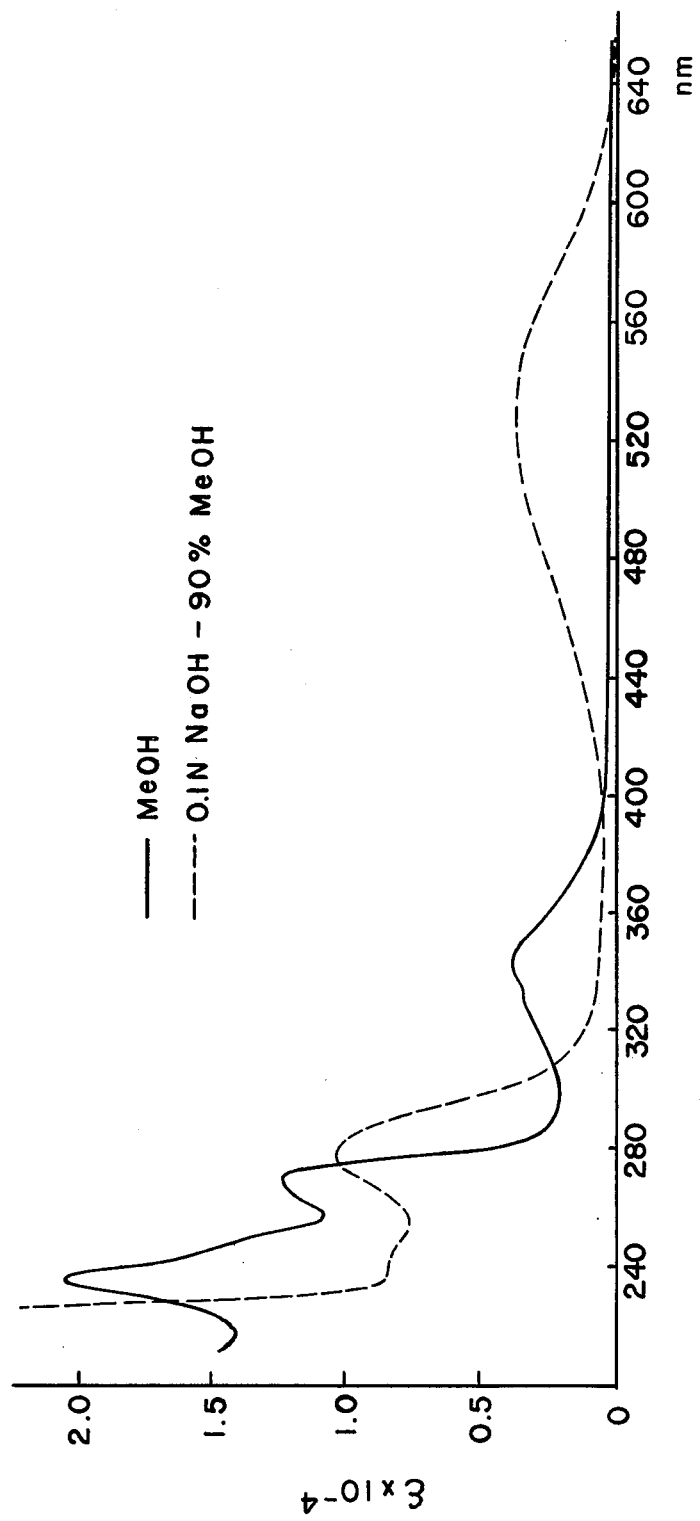
Figure 8:
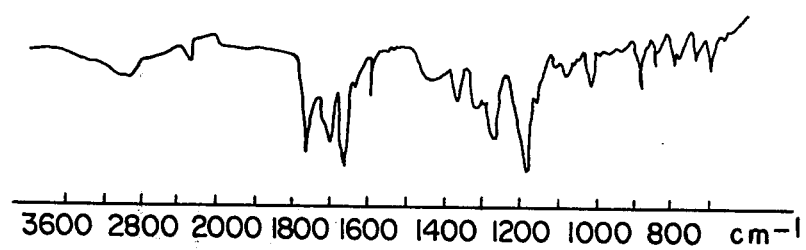
Figure 10:
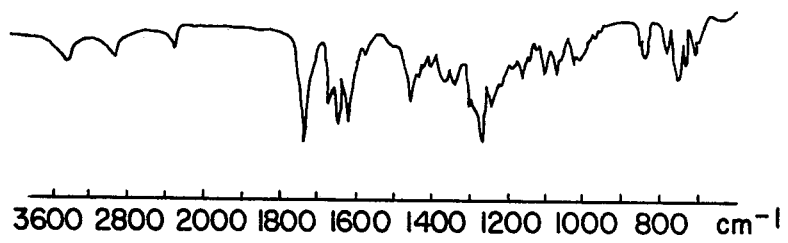
Figure 9:
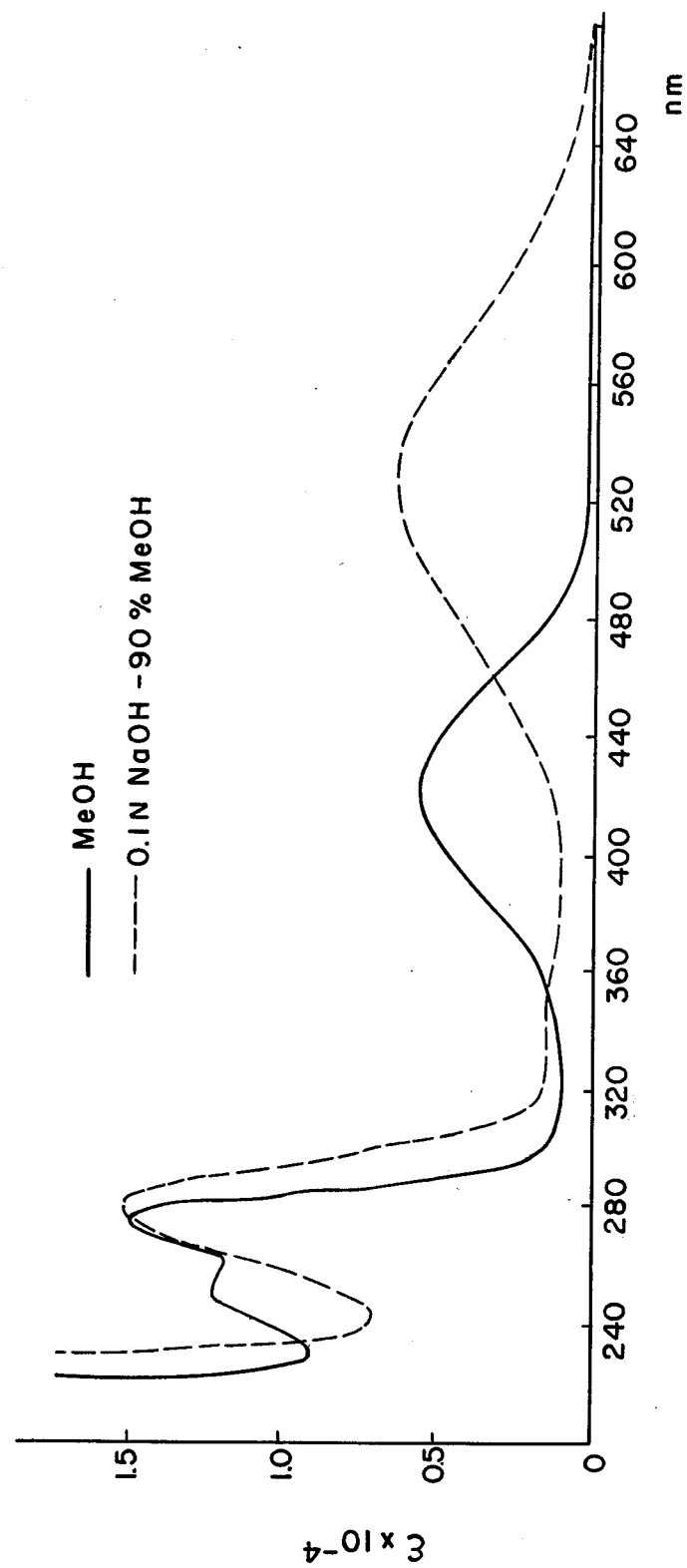

FIG. 3—ORD curves of (I) nanaomycin A, (II) kalafungin and (III) deoxyfrenolicin FIG. 4—UV absorption spectrum of nanaomycin C FIG. 5—IR absorption spectrum of nanaomycin C FIG. 6—NMR spectrum of nanaomycin C FIG. 7—UV absorption spectrum of acetylnanaomycin A FIG. 8—IR absorption spectrum of acetylnanaomycin A FIG. 9—UV absorption spectrum of nanaomycin A methyl ester FIG. 10—IR absorption spectrum of nanaomycin A methyl ester Nanaomycin A and derivatives thereof according to the present invention are active upon mycoplasma, Gram-positive bacteria and tricophyton, and the acute toxicity (LD$_{50}$, intra-penetrial injection) in mice of nanaomycin A is 28.2 mg/Kg. These compounds have a excellent therapeutic effect on infectious diseases caused by a parasite of Gram-positive bacteria, trichophyton or mycoplasma. It has now been found that the properties of nanaomycin A and derivatives thereof according to the present invention are different from those of known antibiotics such as deoxyfrenolicin and ethylkalafunginate (ethylkalamycin).

Nanaomycin A is in the form of crystals of yellow needles and has the following physical and chemical characteristics:

1. Elementary analysis: Found: C—63.35%; H—4.47%; N—0%. Calculated (as C$_{16}$H$_{14}$O$_6$): C—63.57%; H—4.66%; N—0%.

2. Molecular weight: m/e determined by mass spectrum is 302.084 and the theoretical value of m/e for C$_{16}$H$_{14}$O$_6$ is 302.079.

3. Melting point: 178°–180° C.

4. Specific rotation: $[\alpha]_D^{26}$ —27.5° (C=1.0 in methanol)

5. Ultraviolet absorption spectrum (FIG. 1): $\lambda_{max}^{MeOH}$ nm($\epsilon$): 250 (0.985×10$^4$), 274 (1.22×10$^4$), 423 (0.404×10$^4$)

6. Infrared absorption spectrum (FIG. 2): Relatively strong absorptions at 3150, 2960, 2910, 1725, 1640, 1610, 1450, 1370, 1320, 1270, 1220, 1160 cm$^{-1}$ when measured by KBr method.

7. Solubility: Easily soluble in methanol, ethanol, ethylacetate, chloroform, acetone and ether. Insoluble in n-hexane, petroleum ether and water.

8. Color reaction: Positive in the reactions with ferric chloride and reduction catalyst [Feigl, N., Anal. Chem., 28, 397 (1956)]. Negative in ninhydrin reaction, Sakaguchi reaction, Ehrlich reaction, Fehling reaction and Molish reaction.

From the characteristics stated above, it has been found that nanaomycin A is a new quinone type compound. Nanaomycin A is also distinguishable from kalafungin (kalamycin) and deoxyfrenolicin owing to the difference of the specific rotation and optical rotatory dispersion curve (ORD curve) shown in FIG. 3.

The antimicrobial spectra of nanaomycin A is shown in Table 1.

| Test Organisms | Medium | MIC (μg/ml) |
|---|---|---|
| Bacillus subtilis PCI 219 | N | 7.8 |
| Staphylococcus aureus FDA 209P | N | 3.9 |
| Staphylococcus aureus FDA 209P(JC-1) | N | 2.0 |
| Sarcina lutea PCI 1001 | N | 2.0 |
| Mycobacterium smegmatis | N | 62.5 |
| Escherichia coli NIHJ | N | 31.3 |
| Escherichia coli NIHJ(JC-2) | N | 250 |
| Klebsiella pneumoniae PCI 602 | N | 31.3 |
| Salmonella typhimurium | N | 62.5 |
| Shigella flexneri | N | 31.3 |
| Xanthomonas oryzae N-5824 | N | 62.5 |
| Pseudomonas aeruginosa | N | 500 |
| Candida albicans | P | 31.2 |
| Saccharomyces sake | P | 31.2 |
| Aspergillus niger ATCC 6275 | P | 62.5 |
| Aspergillus fumigatus IAM 2612 | P | 12.5 |
| Piricularia oryzae | P | 7.8 |
| Microsporum gypseum 704 | P | 0.8 |
| Trichophyton asteroides | P | 1.6 |
| Trichophyton ferrugineum | P | 1.6 |
| Trichophyton interdigitale | P | 1.6 |
| Trichophyton mentagrophytes | P | 0.8 |
| Trichophyton pedis 804 | P | 0.2 |
| Trichophyton purpureum | P | 3.1 |
| Trichophyton roseum | P | 0.4 |
| Trichophyton rubrum | P | <0.1 |
| Trichophyton schoenleini | P | 0.2 |
| Trichophyton violaceum | P | 0.4 |
| Mycoplasma gallisepticum KP-13 | H | <0.013 |
|  | E | 0.05 |
| Mycoplasma gallisepticum S-6 | H | <0.013 |
|  | E | 0.10 |
| Mycoplasma gallisepticum 3-3P | H | <0.013 |
| (Spiramycin resistant) | E | <0.013 |
| Mycoplasma gallinarum | H | 1.56 |
| Mycoplasma iners | H | 3.12 |

-continued

| Test Organisms | Medium | MIC (μg/ml) |
|---|---|---|
| Mycoplasma pneumoniae | E | 0.013 |
| Acholeplasma laidlawii (A) PG8 | H | >25 |
|  | E | >25 |
| Acholeplasma laidlawii (B) Bml | H | 25 |
|  | E | >25 |

Note:
Medium N-nutrient agar (pH 7.0, 2 days, 37° C.)
P-potato agar (pH 6.4, 4 days, 27° C.
H-Hokken PPLO agar (pH 7.8, 8 days, 37° C.)
E-Eiken PPLO agar (pH 7.8, 8 days, 37° C.)
MIC-Minimal inhibitory concentration As apparent from Table 1, nanaomycin A exhibits a strong activity against Gram-positive bacteria. For example, the growth of *Staphylococcus aureus* is inhibited at a concentration of 2.0 to 8.0 μg/ml and the growth of some fungi belonging to the genus Trichophyton is inhibited at a concentration of not more than 3.1 μg/ml. Nanaomycin A has also a high activity against mycoplasma and the growth of *Mycoplasma gallisepticum* is inhibited at a concentration of not more than 0.1 μg/ml.

*phytes* at the back of guinea pigs is treated with a solution of 0.01-1% nanaomycin A dissolved in propyleneglycolethanol (3:1 v/v) once daily for 8 days, an excellent therapeutic effect on erythema and scales is observed. Furthermore, nanaomycin A has a therapeutic effect on infectious diseases of animals caused by a parasite of the genus Mycoplasma and exhibits therapeutic effect on chronic respiratory disease of chickens caused by *Mycoplasma gallisepticum*.

When dermatomycosis of cattle caused by mass infection of *Trichophyton verrucosum* is treated with nanaomycin A, nanaomycin A is dissolved or suspended in a suitable carrier, for example, olive oil, and is coated on the affected part directly with or without removal of the scales. SP-Burton (a commercial product available from Rakuno-shinko K.K., Japan) which is considered as a most effective agent for dermatomycosis of animals is used as a control therapeutic agent. The therapeutic effects are observed for 4 weeks. The results obtained by once-coating of nanaomycin A and by twice-coating (the second coating is carried out a week after the first coating) are shown in Tables 2 and 3, respectively.

Table 2

|  | Agent | Con. mg/ml | Sample | Result AFTER |  |  |  |
|---|---|---|---|---|---|---|---|
|  |  |  |  | 1 week | 2 weeks | 3 weeks | 4 weeks |
| I | Nanaomycin A | 0.1 | 1 | ++ | ++ | +++ | +++ |
|  | Nanaomycin A | 1 | 1 | +++ | +++ | +++ | +++ |
|  | Nanaomycin A | 10 | 1 | +++ | +++ | +++ | +++ |
|  | SP-Burton | 0.3 | 1 | — | — | — | — |
| II | Nanaomycin A | 0.1 | 1 | +++ | +++ | +++ | +++ |
|  | Nanaomycin A | 1 | 1 | +++ | +++ | +++ | +++ |
|  | Nanaomycin A | 10 | 1 | +++ | +++ | +++ | +++ |
|  | SP-Burton | 0.3 | 1 | +++ | + | — | — |

Table 3

|  | Agent | Con. mg/ml | Sample | Results AFTER |  |  |  |
|---|---|---|---|---|---|---|---|
|  |  |  |  | 1 week | 2 weeks | 3 weeks | 4 weeks |
| I | Nanaomycin A | 0.1 | 1 | ++ | +++ | +++ | +++ |
|  | Nanaomycin A | 1 | 1 | ++ | ++ | +++ | +++ |
|  | Nanaomycin A | 10 | 1 | +++ | +++ | +++ | +++ |
|  | SP-Burton | 0.3 | 1 | — | — | — | — |
| II | Nanaomycin A | 0.1 | 1 | +++ | +++ | +++ | +++ |
|  | Nanaomycin A | 1 | 1 | +++ | +++ | +++ | +++ |
|  | Nanaomycin A | 10 | 1 | +++ | +++ | +++ | +++ |
|  | SP-Burton | 0.3 | 1 | +++ | ++ | + | — |

Note for Tables 2 and 3:
I: direct coating on affected part
II: coating after removing the scales of affected part
Cond.: concentration of agent
+++: complete removal of scales and recovered
++: a little scales remained
+: removal of a part of scales
= no removal of scale and no recovery Furthermore, nanaomycin A exhibits a strong activity against a spiramycin-resistant *Mycoplasma gallisepticum*.

Nanomycin A exhibits an excellent therapeutic effect on various infectious diseases of animals caused by a parasite of the genus Trichophyton. For example, when dermatomycosis caused by *Tricophyton metagor-*

The anti-fungal activity and antimycoplasma activity of nanaomycin A are shown in Tables 4 and 5, respectively.

Table 4

| | Antifungal Activity | | |
|---|---|---|---|
| | Minimal Inhibitory Con. (μg/ml) | | |
| Test Organisms | Nanaomycin A | Y | Z |
| *Candida albicans* | 50 | 50 | >100 |
| *Saccharomyces sake* | 12.5 | 6.3 | >100 |
| *Aspergillus fumigatus* | 6.3 | 6.3 | >100 |
| *Aspergillus niger* | 25 | >100 | >100 |
| *Microsporum gypseum* | 0.8 | <0.2 | >100 |
| *Trichophyton asteroides* | 0.8 | <0.2 | >100 |
| *Trichophyton ferrugineum* | 0.8 | 3.1 | >100 |
| *Trichophyton interdigitale* | 1.6 | 0.4 | >100 |
| *Trichophyton rubrum* | <0.2 | <0.2 | >100 |
| *Trichophyton schoenleini* | <0.2 | <0.2 | >100 |
| *Trichophyton violaceum* | 3.1 | 0.3 | >100 |

Note:
Minimal inhibitory concentration was assayed by agar dilution method (potato agar, pH 6.4, 27° C., 4 days).
Y: deoxyfrenolicin
Z: ethylkalafunginate (ethylkalamycinate)

Table 5

| | Antimycoplasma Activity | |
|---|---|---|
| Antibiotic | Concentration (μg/ml) | Inhibitory Zone (mm) |
| Nanaomycin A | 10 | 20.4 |
| | 100 | 28.7 |
| Deoxyfrenolicin | 10 | 14.6 |
| | 100 | 21.8 |
| Ethylkalafunginate | 10 | none |
| | 100 | none |

Note:Inhibitory zone is assayed by paper disc method (Eiken PPLO agar, pH 7.8, 37° C., 1 day).

As shown in Table 5, the antimycoplasma activity of nanaomycin A is superior to those of deoxyfrenolicin and ethylkalafunginate.

Further study of nanaomycins has now led to the discovery of some nanaomycin derivatives, namely nanaomycin C, acetylnanaomycin A and nanaomycin A methyl ester, having similar properties to those of nanaomycin A. The derivatives of nanaomycin A according to the present invention have the following physical and chemical properties.

(A) Nanaomycin C

Nanaomycin C is neutral and in the form of crystals of orange needles.

1. Elementary analysis: Found: C—63.46%; H—4.50%; N—4.89%. Calculated (as $C_{16}H_{15}NO_5$): C—63.78%; H—4.64%; N—5.02%.
2. Molecular weight: m/e determined by mass spectrum is 301.092 and the theoretical value of m/e for $C_{16}H_{15}NO_5$ is 301.095.
3. Melting point: 222°–224° C. (decomposition)
4. Specific rotation: $[\alpha]_D^{26} -2°$ (C=0.5 in dioxane)
5. Ultraviolet absorption spectrum (FIG. 4): $\lambda_{max}$-$^{MeOH}$nm(ε): 248 (10100), 274 (12400), 424 (4610)
6. Infrared absorption spectrum (FIG. 5): Relatively strong absorptions at 3400, 3260–70, 3180, 2960, 2910, 1645, 1605, 1570, 1450, 1420, 1392, 1360, 1315, 1278, 1263, 1233, 1210, 1160 and 1103 cm$^{-1}$ when measured by KBr method.
7. Solubility: Soluble in methanol, ethanol, ethylacetate, chloroform and acetone. Insoluble in water, n-hexane, and petroleum ether.
8. Color reaction: Positive in the reactions with ferric chloride, 2,4-dinitrophenyl hydrazine and formaldehyde-O-dinitrobenzene. Negative in ninhydrin reaction, Ehrlich reaction and Sakaguchi reaction.
9. Rf value: 0.35 in silica gel thin-layer chromatography using chloroform-methanol (10:1 v/v).
10. Nuclear magnetic resonance (NMR) spectrum: Shown in FIG. 6.

From the characteristics stated above, it has been found that nanaomycin C is a new compound similar to nanaomycin A and is an acid amide of nanaomycin A.

(B) Acetylnanaomycin A

Acetylnanaomycin A is in the form of crystals of pale yellow needles.

1. Elementary analysis: Found: C—62.89%; H—4.73%; N—0%. Calculated (as $C_{18}H_{16}O_7$): C—62.79%; H—4.68%; N—0%.
2. Molecular weight: m/e determined by mass spectrum is 344.089 and the theoretical value of m/e for $C_{18}H_{16}O_7$ is 344.090.
3. Melting point: 190°–192° C.
4. Specific rotation: $[\alpha]_D^{22} +32.4°$ (C=1.02, CHCl$_3$)
5. Ultraviolet absorption spectrum (FIG. 7): $\lambda_{max}$-$^{MeOH}$ nm(ε): 235 (20700), 265 (12100), 270 (12300), and 342 (3750)
6. Infrared absorption spectrum (FIG. 8): Relatively strong absorptions at 1765, 1700, 1670 cm$^{-1}$ when measured by KBr method.
7. Solubility: Soluble in methanol, ethanol, ethylacetate, chloroform, acetone and ether. Insoluble in n-hexane, petroleum ether and water.
8. Color reaction: Positive reaction to reduction catalyst [Feigl, N., Anal. Chem., 28, 397 (1956)]. Negative in ninhydrin reaction, Sakaguchi reaction, Ehrlich reaction, Fehling reaction and Molish reaction.

From the characteristics stated above, it has been found that acetylnanaomycin A is a new compound similar to nanaomycin A.

(C) Nanaomycin A methyl ester

1. Elementary analysis: Found: C—64.84%; H—5.21%; N—0%. Calculated (as $C_{17}H_{16}O_6$): C—64.55%; H—5.10%; N—0%.
2. Molecular weight: m/e determined by mass spectrum is 316.092 and the theoretical value of m/e for $C_{17}H_{16}O_6$ is 316.090.
3. Melting point: 99°–102° C.
4. Specific rotation: $[\alpha]_D^{20} -12.7°$ (C=1.02, CHCl$_3$)
5. Ultraviolet absorption spectrum (FIG. 9): $\lambda_{max}$-$^{MeOH}$ nm(ε): 248 (12400), 274 (15100), and 424 (5650)
6. Infrared absorption spectrum (FIG. 10): Characteristic and relatively strong absorptions at 1730, 1645 and 1615 cm$^{-1}$.
7. Solubility: Soluble in methanol, ethanol, ethylacetate, chloroform, acetone and ether. Insoluble in n-hexane, petroleum ether and water.
8. Color Reaction: Positive reactions to ferric chloride and reduction catalyst [Feigl. N., Anal. Chem., 28, 397 (1956)]. Negative in ninhydrin reaction, Sakaguchi reaction, Ehrlich reaction, Fehling reaction and Molish reaction.

From the characteristics stated above, it has been found that nanaomycin A methyl ester is a new compound similar to nanaomycin A.

The antimicrobial activities of the derivatives of nanaomycin A are shown in Tables 6–8.

Table 6
Minimal Inhibitory Concentration of Nanaomycin C

| Test Organisms | Medium | (μg/ml) |
|---|---|---|
| Staphylococcus aureus FDA 209P | N | 6.3 |
| Staphylococcus aureus FDA 209P (JC-1) | N | 3.1 |
| Bacillus subtilis PCI 219 | N | 6.3 |
| Sarcina lutea PCI 1001 | N | 25 |
| Mycobacterium smegmatis ATCC 607 | N | 50 |
| Escherichia coli NIHJ | N | 100 |
| Escherichia coli NIHJ (JC-2) | N | >100 |
| Klebsiella pneumoniae PCI 602 | N | >100 |
| Salmonella typhimurium | N | >100 |
| Shigella flexneri | N | >100 |
| Pseudomonas aeruginosa | N | >100 |
| Candida albicans | P | >100 |
| Saccharomyces sake | P | >100 |
| Aspergillus niger | P | >100 |
| Trichophyton interdigitale | P | 100 |
| Schlerotinia cinerea | P | 100 |
| Mycoplasma gallisepticum KP-13 | E | 12.5 |
| Mycoplasma gallisepticum S-6 | E | 6.3 |
| Mycoplasma gallisepticum 333P (Spiramycin resistant) | E | 3.1 |
| Mycoplasma gallinarum | E | 12.5 |
| Mycoplasma iners | E | 50 |
| Mycoplasma pneumoniae | E | 6.3 |

Note: N-nutrient agar (pH 7.0, 2 days, 37° C.)
P-potato agar (pH 6.4, 4 days, 27° C.)
E-Eiken PPLO agar (pH 7.8, 8 days, 37° C.)

Table 7
Minimal Inhibitory Concentrations of Acetylnanaomycin A and Nanaomycin A methyl ester

| Test organisms | Med. | MIC (~g/ml) I | II | Control |
|---|---|---|---|---|
| Staphylococcus aureus FDA 209P | N | 1.6 | 12.5 | 3.9 |
| Staphylococcus aureus FDA 209P (JC-1) | N | 0.8 | 25 | 2.0 |
| Staphylococcus aureus FS 1227 (PC-R) | N | 0.8 | 25 | 1.6 |
| Staphylococcus aureus KB 61 (R-TC, EM) | N | 0.8 | 12.5 | 1.6 |
| Staphylococcus aureus KB 64 (R-TC, EM) | N | 0.4 | 12.5 | 0.8 |
| Bacillus subtilis PCI 219 | N | 3.1 | 25 | 6.3 |
| Bacillus cereus T | N | 25 | 25 | 12.5 |
| Sarcina lutea PCI 1001 | N | 1.6 | 25 | 1.6 |
| Corynebacterium paurometabolum | N | 6.3 | 25 | 12.5 |
| Mycobacterium smegmatis ATCC 607 | N | 50 | 12.5 | 100 |
| Aerobacter aerogenes IAM 1183 | N | >100 | >100 | >100 |
| Proteus vulgaris IFO 3167 | N | 50 | >100 | 50 |
| Proteus mirabilis | N | >100 | >100 | >100 |
| Escherichia coli NIHJ (JC-2) | N | >100 | >100 | >100 |
| Salmonella typhimurium | N | 50 | >100 | 100 |
| Shigella sonnei E 33 | N | 100 >100 | 100 | |
| Pseudomonas aeruginosa P-3 | N | >100 | >100 | >100 |
| Candida albicans | P | 25 | >100 | 50 |
| Saccharomyces sake | P | 12.5 | 50 | 12.5 |
| Piricularia orizae | P | 0.8 | 12.5 | 0.8 |
| Aspergillus niger ATCC 6275 | P | 25 | >100 | 25 |
| Aspergillus fumigatus IAM 2162 | P | 6.3 | 100 | 6.3 |
| Microsporum gypseum 704 | P | 0.4 | 1.6 | 0.8 |
| Trichophyton asteroides | P | 0.8 | 12.5 | 0.8 |
| Trichophyton ferrugineum | P | 0.8 | 12.5 | 0.8 |
| Trichophyton interdigitale | P | 1.6 | 12.5 | 1.6 |
| Trichophyton mentagrophytes | P | 0.4 | 6.3 | <0.2 |
| Trichophyton pedis 804 | P | 0.8 | 12.5 | 0.8 |
| Trichophyton purpureum | P | 1.6 | 12.5 | 0.4 |
| Trichophyton roseum | P | 0.4 | 0.8 | <0.2 |
| Trichophyton rubrum | P | <0.2 | <0.2 | <0.2 |
| Trichophyton schoenleini | P | <0.2 | <0.2 | <0.2 |
| Trichophyton violaceum | P | 0.8 | 12.5 | 3.1 |

Note: N-nutrient agar (pH 7.0, 2 days, 37° C.)
P-potato agar (pH 6.4, 4 days, 27° C.)
R-Resistant strain
PC-penicillin
TC-tetracyclin
EM-erythromycin
I-acetylnanaomycin A
II-nanaomycin A methyl ester
Control-nanaomycin A

Table 8
Antimycoplasma Activities of Acetylnanaomycin A and Nanaomycin A Methyl Ester

| Test Organism | Med. | Inhibition Zone (mm) I | II | A |
|---|---|---|---|---|
| Mycoplasma gallisepticum KP-13 | E | 28.5 | 28.5 | 28.7 |
| Acholeplasma laidlawii (A) | H | none | none | none |

Note:
E-Eiken PPLO agar (pH 7.8, 8 days, 37° C.)
H-Hokken PPLO agar (pH 7.8, 8 days, 37° C.)
I-Acetylnanaomycin A
II-Nanaomycin A methyl ester
A-Nanaomycin A Nanaomycin C inhibits mainly Gram-positive bacteria and mycoplasmas, and exerts as strong activity against Gram-positive bacteria as nanaomycin A, but a weaker activity against fungi and mycoplasmas than nanaomycin A.

Acetylnanaomycin A exerts a strong activity against Gram-positive bacteria than nanaomycin A and exerts as strong activity against fungi and mycoplasmas as nanaomycin A. The acute toxicity ($LD_{50}$, intra-penetrial injection) in mice of acetylnanaomycin A is 38.5 mg/Kg which is lower than that of nanaomycin A.

Antimicrobial activity of nanaomycin A methyl ester is generally lower than those of other derivatives of nanaomycin A.

Therapeutic effect of the derivatives of nanaomycin A of this invention are determined in a similar manner to that applied to nanaomycin A on infectious diseases caused by a parasite of the genus Tricophyton in guinea pigs and cattle. Acetylnanaomycin A exhibits superior therapeutic effect to nanaomycin A when its concentration is 0.01–1%. The therapeutic effect of nanaomycin A methyl ester is inferior to those of nanaomycin A and acetylnanaomycin A. Nanaomycin C exhibits a poor therapeutic effect on infectious diseases caused by a parasite of the genus Trichophyton.

According to another aspect of the present invention, there is provided a process for producing nanaomycins A and C by fermentation, in which a microorganism which belongs to the genus Streptomyces and which is capable of producing nanaomycins A and/or C is cultured aerobically in a medium conventionally used for fermentation of microorganisms belonging to the genus Streptomyces to accumulate nanaomycins A and/or C in the cultured broths and nanaomycins A and/or C accumulated are recovered therefrom For the purpose of the present invention, it is possible to use not only the hereinafter described *Streptomyces rosa* var. *notoensis* and any mutant obtained therefrom but also any strain which belongs to the genus Streptomyces and which is capable of producing nanaomycins A and/or C. The microbiological characteristics of a preferable strain *Streptomyces rosa* var. *notoensis* which is used in the following examples to produce nanaomycins A and/or C are as follows:

1. Morphological characteristics:
   Forming abundantly aerial mycelium on both synthetic and natural agar media, the ending of which forming massy or irregular spiral. Conidiophore formed on aerial mycelium. Conidiospores are oval (0.6–1.0μ) and in a chain of 10 or more. The spores have smooth surfaces.
2. Cultural characteristics: Shown in Table 9.
3. Physiological characteristics:
   Growth temperature: 15°–45° C.
   Liquefaction of gelatin: positive
   Hydrolyzation of starch: positive
   Coagulation of skim milk: positive
   Peptonization of skim milk: positive
   Formation of melanoid pigment: negative
   Formation of tyrosinase: negative
   Reduction of nitrate: positive
   Formation of hydrogen sulfide: negative
   Decomposition of cellulose: negative
4. Usability of various carbon sources: Arabinose, xylose, glucose, fructose, rhamnose, mannitol, glycerol, maltose and mannose may be usable. Sucrose, innositol and raffinose may be unusable.

Table 9

Cultural Characteristics of *S. rosa* var. *notoensis* (FERM 2209)

| Medium | Growth | Reverse | Aerial mycelium | Soluble pigment |
|---|---|---|---|---|
| Sucrose-nitrate agar | good, light ivory to light melon yellow | light melon yellow to apricot | light apricot | pearl pink to light melon yellow |
| Glucose-nitrate agar | good, dusty yellow to golden brown | golden brown to chocolate brown | white to pearl pink | light wheat to sepia brown |
| Glycerol-asparagine agar | good, light melon yellow to orange rust | apricot | light apricot | melon yellow to apricot |
| Inorganic salts-starch agar | moderate, light melon yellow | pearl pink to golden brown | white to flesh pink | dark luggage tan to sepia brown |
| Tyrosine agar | good, light wheat to amber topaz | light melon yellow to nude tan | light melon yellow to pearl pink | light wheat to melon yellow |
| Nutrient agar | moderate, colorless to pearl pink | squash yellow to bright yellow | white, scant | none |
| Glucose-peptone agar | moderate, colorless to golden brown | golden brown to sepia brown | white | ivy to dark laurel |
| Yeast extract-malt extract agar | good, colorless to golden brown | golden brown to orange rust | light melon yellow to light apricot | ivy |
| Oatmeal agar | moderate, colorless to light melon yellow | light melon yellow to nude tan | light melon yellow to light apricot | light tan |
| Peptone-yeast extract from agar | moderate, cream to light wheat | colonial yellow | scant, white to colonial yellow | none |
| Tryptone-yeast extract broth | surface growth, moderate, light ivory | light ivory | white | none |
| Milk | pearl pink | | none | light apricot to pearl pink |
| Gelatin | surface growth, good | pearl pink to chartreuse tint | white to celadon gray | laurel |
| Nitrate broth | surface growth, moderate | light ivory | white | none |
| Cellulose | none | none | none | none |

The microbiological characteristics of this strain are summarized as follows:

Conidiophore is spiral and conidiospore is smooth. Growth on synthetic medium is colored in yellowish gray or orange gray or reddish brown, and the formed aerial mycelium is colored in white or orange gray or pink. There is formed a soluble pigment colored in yellowish brown or dark reddish brown. When an organic medium is used, the growth is generally colorless or colored in orange gray or brown, and the formed mycelium is colored in white or orange gray or pink. Sometimes soluble pigment is not formed, while a greenish gray or grayish black pigment is formed in some media. This strain is non-chromogenic and has a relatively high activity with regard to the decomposition of protein and starch.

With respect to the strains having the afore-mentioned characteristics, a search was made for strains having analogous characteristics to those of the strain used in the following examples with reference, for example, to "The Actinomycetes" by S. A. Waksman, Vol. 2 (1961) and "Cooperative Description of Type Strains of Streptomyces" by E. B. Shirling and D. Gottlieb [International Journal of Systematic Bacteriology, Vol. 18, No. 2, pages 69–189 (1968): Vol. 18, No. 4, pages 279–392 (1969); Vol. 19, No. 4, pages 391–512 (1969); and Vol. 22, No. 4, pages 265–394 (1972)]. As a result, some species designated as "fradiae" i.e. *Streptomyces fradiae*, *Streptomyces luridus*, *Streptomyces roseus*, *Streptomyces fuscus*, *Streptomyces roseoluteus*, and *Streptomyces rosa* were found as being analogous. Among them, *Streptomyces roseoluteus* and *Streptomyces rosa* are indeed likely to be most analogous. However, on one hand *Streptomyces roseoluteus* is distinguishable from the nanaomycin-producing strain of the present invention because the color at the reverse side of *S. roseoluteus*'s colony becomes yellowish orange from yellow in certain media such as for example of yeast extract-malt extract, oat meal agar, inorganic starch agar as well as of glycerol-asparagine agar, with simultaneously formation of yellowish soluble pigment. On the other hand, *Streptomyces rosa* is generally similar to the nanaomycin-producing strain according to the present invention with the exception that the production of soluble pigment in certain media such as for example of yeast extract-malt extract agar, glucose-peptone agar and that the reduction of nitrate is not observed in the case of Streptomyces rosa. Accordingly, this strain is designated as *Streptomyces rosa* var. notoensis.

The nanaomycin-producing strain used in the following examples produces simultaneously in the cultured broths nanaomycins A and C and nanaomycin B represented by general formula:

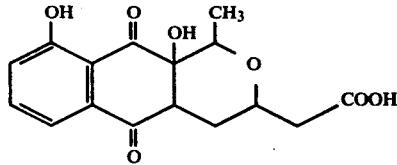

and referred to in the related U.S. patent application Ser. No. 719,752, filed Sept. 2, 1976, now abandoned.

The strain used in the following examples has been deposited on an unrestricted basis with the Fermentation Research Institute, Agency of Industrial Science and Technology, Japanese Government and assigned an accession number of FERM-P No. 2209.

According to the process of the present invention, either any synthetic or organic medium may be used when it contains a suitable carbon source, nitrogen source, inorganic substances and, if desired, various other nutrients. Various carbon and nitrogen sources may be used when these sources are adaptable for the strain in use.

More concretely, the useful carbon sources are exemplified by various carbohydrates such as glucose, glycerol, fructose, maltose, mannitol, xylose, galactose, lactose, ribose, starch and starch hydrolyzate. The concentration of carbon source is preferably 0.05–5.0%, (when calculated as glucose) based upon the medium. It is also possible to use organic acids such as, for example, gluconic acid, pyruvic acid, lactic acid, acetic acid; and various amino acids such as glycine, glutamic acid, alanine etc.

As the nitrogen source, it is possible to use, for example, ammonia; various inorganic and organic ammonium salts such as ammonium chloride, ammonium phosphate, ammonium sulfate, ammonium nitrate; nitrogen-containing organic materials such as urea, peptone, NZ-amine, meat extract, dried yeast, yeast extract, corn steep liquor, casein hydrolyzate, fish meal, digested product thereof, soybean meal, digested products thereof, defatted soybean, digested products thereof, pupa hydrolyzate, and various amino acids such as glycine, glutamic acid, alanine etc.

As the inorganic substance, it is possible to use, for example, various phosphates, magnesium sulfate etc. If desired, it is also possible to use a trace amount of heavy metal salts, which is, however, not always essential when the medium used contains natural materials. In case a mutant strain having a nutritional requirement is used, it is necessary to add the required substance to the medium.

Liquid medium is preferable for producing large amount of nanaomycins A, B and C though solid medium may be used. It is possible to use a seed medium having a similar composition to that of the main culture medium, and the seed is preferably obtained by fermentation carried out aerobically at a temperature of 27° C. for two days, for example, by using a Sakaguchi flask.

The fermentation is carried out aerobically with shaking and/or submerged conditions at a temperature of from 15° to 40° C. at an adjusted pH of 6–10 for about 2–8 days, whereby large amounts of nanaomycins A, B and C are accumulated concurrently in the medium and microbial body. After completion of the fermentation, nanaomycins A, B and C are recovered from the cultured broths. For example, the broths are separated into the microbial body and filtrate. The filtrate is adjusted to an acidic pH (preferably from 2 to 4) with HCl or the like and is then subjected to extraction with a suitable organic solvent such as e.g. ethyl acetate or butyl acetate. After this, nanaomycins A, B and C are obtained by purifying the extracted substance in a conventional manner which would be used for the purification of known substances soluble in organic solvents.

According to the present invention, preferable methods for the fermentation are exemplified as follows:

A culture medium (100 ml) is put in a 500 ml Sakaguchi flask and sterilized at a temperature of 120° C. for 15 minutes. After this, spores and/or mycelium of the used strain are inoculated and the fermentation is effected with shaking (110 r.p.m.) at a temperature of 27° C. for a sufficient period of time (e.g. for 3 days) to accumulate large amounts of nanaomycins A, B and C in the culture broths.

Alternatively, a culture medium (20 liters) is put into a 30-liter jar fermentor and sterilized at a temperature of 120° C. for 15 minutes. After this, a seed culture is inoculated and the fermentation is effected at a temperature of 27° C. for 3 days with shaking (300 r.p.m.) and aeration (10 l/min). It is also preferred to culture using a medium (200 ml) in a tank-type fermentor (capacity—400 liters) at a temperature of 27° C. for 3 days with shaking (200 r.p.m.) and aeration (100 l/min).

In either case, good results can be obtained by using glycerine and soybean meal as the carbon and nitrogen sources, respectively. A medium containing glycerine (2.0%) soybean meal (2.0%) and NaCl (0.3%) and having a pH of 7.0 is particularly advantageous. In one embodiment using this medium, an inhibition zone (diameter—30 cm) is observed in the supernatant of the cultured liquor at a pH of 5.2 after culturing at a temperature of 27° C. for 70 hours by using a tank-type fermentor. Although nanaomycins A, B and C are found in both the fermented liquid and solid materials, the former contains usually larger amounts of nanaomycins A, B and C than the latter.

After completion of the fermentation, nanaomycins A and C are recovered from the cultured broths in the following manner:

The cultured broths are separated into solid and liquid phases in conventional manner by means of filtering, centrifuging and the like. The liquid phase, i.e. the filtrate is adjusted to an acidic pH (preferably from 2 to 4) with HCl or the like and is then subjected to extraction with a suitable organic solvent such as e.g. ethyl acetate or butyl acetate. After this, nanaomycins are obtained by purifying the extracted substance in a conventional manner which is applicable for the purification of known substances soluble in organic solvents.

It is also possible to isolate nanaomycins from the extracted solution in an acidic condition. For example, an aqueous solution of sodium bicarbonate (1%) is used to elute nanaomycins A and B from the extract with quick speed. Immediately after this, the eluate containing nanaomycins A and B is adjusted to an acidic pH, for example, with hydrochloric acid, and further extracted with a suitable organic solvent such as, for example ethyl acetate or butyl acetate. The thus-obtained extract is concentrated to dryness, resulting in nanaomycins A and B in the form of crude powders which are then subjected to column chromatography using silica gel, whereby the crude powders containing nanaomycins A and B are developed with a solvent system of benzene-acetone (4:1 v/v) to elute the fractions containing nanaomycin A followed by nanaomycin B-containing fractions. The thus-obtained fractions are separately combined and concentrated to dryness. The dried material containing nanaomycin A is dissolved in ethanol which is then added with a small amount of water to give nanaomycin A in the form of needle crystals. Nanaomycin B can also be purified in a similar manner to that applied to nanaomycin A.

In the recovery, nanaomycins A and B are eluted from the ethyl acetate layer with 1% of sodium bicarbonate, while nanaomycin C remains in the layer because nanaomycin C is neutral, which is then concentrated under reduced pressure to dryness to obtain the crude powders of nanaomycin C. The crude powders are chromatographed on a column of silica gel with chloroform-methanol (50:1 v/v). The fractions containing nanaomycin C are concentrated under reduced pressure to dryness to obtain crude powders of nanaomycin C which are extracted with ethyl acetate and then recrystallized from an ethyl acetate to obtain orange crystals of nanaomycin C.

Nanaomycin A is also obtained from nanaomycin B (hereinbefore referred to) in an alkaline medium in the following manner:

Nanaomycin B (200 mg) is dissolved in 60 ml of 0.1 N sodium hydroxide and the solution is allowed to stand for 10 minutes. After adjusting to pH 2.0 with 6 N hydrochloric acid, the product is extracted with ethyl acetate. The extract is evaporated and orange yellow needles are obtained from an ethanol solution of the product. The compound is identified as nanaomycin A by the melting point, IR spectrum and thin-layer chromatography.

According to the present invention, acetylnanaomycin A and nanaomycin A methyl ester can be obtained in the following manner:

Nanaomycin A is left in a solution containing acetic anhydride and pyridine, poured onto a mixture of ice and hydrochloric acid, and is then extracted with chloroform. The extract is washed with water, dried, and then recrystallized from benzene to obtain acetylnanaomycin A in the form of crystals of pale yellow needles.

Nanaomycin A is dissolved in ether and treated with an ethereal solution of diazomethane. After removal of the solvent a column chromatography on silica gel with a chloroform-methanol system gives orange-yellow nanaomycin A methyl ester.

Nanaomycin A and derivatives thereof according to the present invention are assayed in a similar manner to that designated as the paper disc method by Itoh, et al [J. of Antibiotics, 24, 855–859 (1971)], for example, as follows:

The strain is cultured at a temperature of 27° C. with shaking. The medium (pH 7.0) contains glycerine (2.0%), soybean meal (2.0%) and NaCl (0.3%). Inhibition zones of a diameter of 17, 27, 28 and 29 mm are observed in the cultured liquor after culturing for 24, 48, 72 and 96 hours, respectively.

The following non-limitative examples illustrate the invention.

EXAMPLE 1

One platinum loop of *Streptomyces rosa* var. notoensis FERM-P No. 2209 capable of producing nanaomycins was taken from a slant culture and inoculated to a seed medium (pH 7.0) for culturing at a temperature of 27° C. for 2 days. The resultant seed culture was further inoculated to a medium (20 liters) put in a 30-liter jar fermentor at a ratio of 1% and cultured at 27° C. for 4 days with aeration (10 l/min) and agitation (300 r.p.m.). These media contained 2.0% of glycerol, 2.0% of soybean meal and 0.3% of NaCl and had an adjusted pH of 7.0. The media were sterilized at a temperature of 120° C. for 15 minutes before use. After completion of the fermentation, the pH of the cultured broths was 4.8 and an inhibition zone against *Mycoplasma gallisepticum* (diameter—30 mm) was observed in the supernatant of the broths. The broths (20 liters) were subjected to centrifugation to remove the mycelium. The filtrate was adjusted to a pH of 2.0 with 6 N HCl and was then subjected to extraction with butyl acetate (4 liters). The butyl acetate layer was extracted with 1% sodium bicarbonate aqueous solution (800 ml). The aqueous layer was adjusted to a pH of 2.0 with 6 N HCl and was subjected to extraction with ethyl acetate. The ethyl acetate layer was concentrated and added with petroleum ether to give yellow-brown powders (1.09 g) which were further purified in the following manner.

The crude powders containing nanaomycins A and B were dissolved in ethyl acetate (15 ml), added with silica-gel (4 g) and then concentrated in vacuo to dryness. The dried material was transferred to a column packed with silica gel (55 g) and developed with a solvent system of benzene-ethyl acetate (4:1 v/v). The eluate was divided into individual fractions (each 15 ml). Each fraction was then assayed by the above-described paper disc method using *Mycoplasma gallisep-*

*ticum* KP-13 as a test microorganism. The first part of the eluate, i.e. Nos. 8 to 22 of the fractions contained nanaomycin A, and No. 14 exhibited a highest activity against the test microorganism. For fractions after No. 30, another solvent system of benzene-ethyl acetate (3:1 v/v) was used as the eluting solution. Nos. 32 to 60 of the divided fractions contained nanaomycin B, and the activity of No. 46 was highest against the control microorganism. The fractions Nos. 8 to 22 were combined and concentrated in vacuo to dryness. The dried solid material was dissolved in ethanol and then added with a small amount of water to give yellow needle crystals (31.7 mg). The crystals were recrystallized from an ethanol solution in a similar manner to that described above to give a purified nanaomycin A (25.3 mg; purity: more than 99%; melting point: 178°–180° C.).

UV absorption spectrum of nanaomycin A: $\lambda_{max}^{MeOH}$ nm: 250, 274 and 423

IR absorption spectrum of nanaomycin A: Characteristic strong abosrptions at 1725, 1640 and 1610 $cm^{-1}$ when measured by KBr method.

The second part of the fractions (Nos. 32 to 60) was combined and concentrated in vacuo to dryness to give pale yellow powders (450 mg). The powders were further subjected to column chromatography using silica gel in a similar manner to that described above to obtain purified powders of nanaomycin B (270 mg; purity: 99%; melting point: 84°–86° C.).

UV absorption spectrum of nanaomycin B: $\lambda_{max}^{MeOH}$ nm: 231 and 352

IR absorbtion spectrum of nanaomycin B: Characteristic strong absorptions at 1705, 1648 and 1605 $cm^{-1}$ when measured by KBr method.

When the butyl acetate layer was extracted with 1% sodium bicarbonate solution as stated above, nanaomycin C was retained in the butyl acetate layer owing to nanaomycin C being neutral. The solvent layer was concentrated and dried to give crude powders (1.3 g) of nanaomycin C which was then chromatographed on a column of silica gel with chloroform-methanol (50:1 v/v). The obtained fractions (each 15 ml) were tested by the above-described paper disc method. Among the total 58 fractions, the fractions of Nos. 51-63 contained nanaomycin C, and the No. 55 fraction exhibited a highest activity against the test microorganism. The fractions containing nanaomycin C were combined and concentrated in vacuo to dryness. The thus obtained solid material (52 mg) was extracted with ethyl acetate and recrystallized from ethyl acetate to give orange-yellow nanaomycin C (35 mg) in the form of needle crystals. Purity: 99% Melting point: 222°–224° C.

UV absorption spectrum of nanaomycin C: $\lambda_{max}^{MeOH}$ nm($\epsilon$): 248 (10100), 274 (12400) and 424 (4610).

IR absorption spectrum:

Characteristic absorptions at 1645 and 1605 $cm^{-1}$.

EXAMPLE 2

To the solid material which was obtained by centrifugation of the cultured broths prepared in a similar manner to that described in Example 1, there was added ethyl acetate (5 liters) with agitation. The thus-obtained extract was added with 1% solution of sodium bicarbonate (2liters) to transfer the material including nanaomycins A and B to the aqueous layer. The aqueous layer was adjusted to a pH of 2.0 with hydrochloric acid and was then subjected to extraction with ethyl acetate (500 ml). The extracted solution was concentrated in vacuo to dryness to give crude powders (521 mg) in yellow brown. The powders were subjected to silica gel column chromatography and the eluate was treated to obtain nanaomycins A and B in a similar manner to that described in Example 1. By extracting with 1% sodium bicarbonate stated above, nanaomycin C-containing ethyl acetate layer was concentrated to dryness to obtain crude powders of nanaomycin C (685 mg). The powders were treated in a similar manner to that described in Example 1 to give a solid material (28.3 mg) from which nanaomycin C was obtained.

|  | Yield | Melting Point | Purity |
|---|---|---|---|
| Nanaomycin A | 13 mg | 173–175° C. | 95% |
| Nanaomycin B | 85 mg | 82–84° C. | 92% |
| Nanaomycin C | 19.7 mg | 220–222° C. | 98% |

EXAMPLE 3

Nanaomycin A (200 mg), which was obtained in a similar manner to that described in Example 1, was left in a solution containing acetic anhydride (2 ml) and pyridine (4 ml) for 16 hours at room temperature. The solution was then poured onto a mixture of ice water and 10% hydrochloric acid and extracted with chloroform (30 ml). The extract was washed with water and concentrated in vacuo to dryness. The thus obtained solid material was recrystallized from benzene to give pale yellow acetylnanaomycin A (145 mg) in the form of needle crystals. Purity—more than 99%; Melting point: 190°–192° C.

UV absorption spectrum: $\lambda_{max}^{MeHO}$ nm($\epsilon$): 235 (20700), 265 (12100), 270 (12300) and 342 (3750).

IR absorption spectrum (by KBr method):

Characteristic absorptions at 1765, 1700 and 1670 $cm^{-1}$.

EXAMPLE 4

Nanaomycin A (200 mg), which was obtained in a similar manner to that described in Example 1, was dissolved in ether (30 ml), added with an excess of an ethereal solution of diazomethane and left for one hour at room temperature. After removing the solvent in vacuo, the reaction material was chromatographed on a column of silica-gel (6 g) with chloroform-methanol (100:1 v/v). The obtained fractions (each 5 ml) were tested by the above-described paper disc method. The fractions of Nos. 5–9 contained nanaomycin A methyl ester, and No. 6 fraction exhibited a highest activity against the test microorganism. The fractions containing nanaomycin A methyl ester were concentrated and dried to obtain orange-yellow powders of nanaomycin A methyl ester (34 mg). Purity: more than 97%. Melting point: 99°–102° C.

UV absorption spectrum: $\lambda_{max}^{MeOH}$ nm($\epsilon$): 248 (12400), 274 (15100), and 424 (5650).

IR absorption spectrum (by KBr method): Characteristic absorptions at 1730, 1645 and 1615 $cm^{-1}$.

What is claimed is:

1. A process for producing by fermentation a nanaomycin compound represented by the general formula (I):

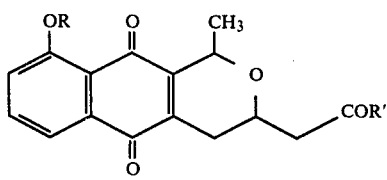

(I)

wherein R is H and R' is selected from the group consisting of OH and NH$_2$, comprising the steps of culturing a microorganism belonging to the genus *Streptomyces rosa* var. *notoensis* in a medium containing sources of carbon, nitrogen and inorganic substances under suitable conditions so as to produce said nanaomycin compound and accumulate same in the culture broth, and recovering said nanaomycin compound therefrom as the principal product.

2. The process of claim 1, in which the strain is *Streptomyces rosa* var. notoensis (FERM-P No. 2209).

3. The process of claim 1, in which the culturing is carried out at a temperature of from 15° to 40° C. at a pH of 6–10 for about 2–8 days.

4. A process for producing by fermentation a nanaomycin compound represented by the general formula (I):

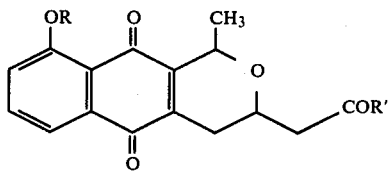

(I)

wherein R is H and R' is selected from the group consisting of OH and NH$_2$, comprising the steps of culturing a microorganism belonging to the genus *Streptomyces rosa* var. *notoensis* in a medium containing sources of carbon, nitrogen, and inorganic substances at a temperature of 15° to 40° C. and a pH of 6 to 10 for about 2 to 8 days so as to produce said nanaomycin compound and accumulate same in the culture broth, and recovering said nanomycin compound therefrom as the principal product.

* * * * *